(12) United States Patent
Yamada et al.

(10) Patent No.: US 6,653,276 B2
(45) Date of Patent: Nov. 25, 2003

(54) HIGH-PURITY CYCLOPENTANE COMPOUND HAVING OXYGEN-CONTAINING GROUP, PROCESS FOR PREPARING SAME, AND PERFUME COMPOSITION

(75) Inventors: Masafumi Yamada, Kawasaki (JP); Hiroshi Fujisawa, Kawasaki (JP)

(73) Assignee: Zeon Corporation, Tokyo (JP)

( * ) Notice: Subject to any disclaimer, the term of this patent is extended or adjusted under 35 U.S.C. 154(b) by 8 days.

(21) Appl. No.: 09/862,346

(22) Filed: May 23, 2001

(65) Prior Publication Data

US 2003/0012799 A1 Jan. 16, 2003

(51) Int. Cl.$^7$ ............................ A61K 7/46; A61K 7/00; A61K 7/06; A61K 7/075; C11D 3/50
(52) U.S. Cl. ............................ 512/1; 424/47; 424/70.1; 424/401; 510/102; 510/105; 510/119; 512/8; 512/14; 512/15; 512/19; 512/25
(58) Field of Search ............................ 512/1, 8, 14, 15, 512/19, 25; 424/401, 47, 70.1; 510/102, 105, 119

(56) References Cited

U.S. PATENT DOCUMENTS

| | | | |
|---|---|---|---|
| 4,217,251 A | 8/1980 | Dastur | .................. 252/522 |
| 5,776,884 A | * 7/1998 | Martin | .................. 512/8 |

FOREIGN PATENT DOCUMENTS

| | | |
|---|---|---|
| EP | 0 770 671 A | 5/1977 |
| EP | 0 016 650 A | 10/1980 |
| EP | 0 366 908 | 9/1990 |

OTHER PUBLICATIONS

Collins et al. ,"The microstructure of poly(cyclopentene) produced by polymerization of cyclopentene with homogeneous Zergler–Natta catalysts", Macromolecules, 1992, 25(1), pp. 233–237.*
R. Mayer: "Synthesen mit Dicarbonsauren, XX. Mitteil: Zur Selbstcondensation des Cyclopentanons" Chemische Berichte vol. 89, No. 6. 1956, XP002181107.
Bulletin De La Societe Chimique De France, 1973, No. 4, p. 1509–1514.
Journal of American Chemical Society, 1994, p. 16, 1962–1972.

* cited by examiner

*Primary Examiner*—S. Mark Clardy
*Assistant Examiner*—Marina Lamm
(74) *Attorney, Agent, or Firm*—Armstrong, Westerman & Hattori, LLP

(57) ABSTRACT

A composition comprising at least 60% by weight, based on the weight of the composition, of a cyclopentanone or cyclopentanol compound having 2,5-dicyclopentylidene substituents, 2,5-dicyclopentyl substituents or 2-cyclopentylidene-5-cyclopentyl substituents. This composition is useful as perfume emitting floral fragrance. 2,5-Dicyclopentylidenecyclopentane (compound 4) is prepared by reaction of 2-cyclopentylidenecyclopentanone with cyclopentanone. 2,5-Dicyclopentylcyclopentanone (compound 5) and 2,5-dicyclopentylidenecyclopentanol (compound 6) are prepared by reduction of compound 4. 2,5-Dicyclopentylcyclopentanol (compound 7) is prepared by reduction of compound 5 or compound 6.

9 Claims, No Drawings

HIGH-PURITY CYCLOPENTANE COMPOUND HAVING OXYGEN-CONTAINING GROUP, PROCESS FOR PREPARING SAME, AND PERFUME COMPOSITION

BACKGROUND OF THE INVENTION (1) Field of the Invention

This invention relates to a composition comprising a cyclopentanone or cyclopentanol compound having cyclopentylidene and/or cyclopentyl substituents at a high concentration, a process for preparing the same, and a perfume composition comprising the same as a fragrant odor-emitting ingredient.

The perfume composition is used, for example, for a perfume, a soap, a shampoo, a hair-treatment, a body shampoo, a detergent, a cosmetic, a hair-spray and an aromatic.

(2) Description of the Related Art

It is known that cyclopentanone derivatives include those which are useful as a perfume. As specific examples of the cyclopentanone derivatives used as a perfume, there can be mentioned methyl 3-oxo-2-(cis-2-pentenyl)-cyclopentaneacetate (trivial name: methyl jasmonate) and methyl 2-pentyl-3-oxocyclopent-1-yl-acetate (trivial name: methyl dihydrojasmonate), which are known as a perfume emitting a jasmine-like floral scent or odor; and 2-cyclopentyl cyclopentylcrotonate which is known as a perfume emitting a fruity and juicy scent or odor. That is, cyclopentanone derivatives having various substituents or functional groups are known as a perfume emitting a fragrant scent or odor.

As a perfume having a cyclopentanone structure with a cyclopentyl derivative substituent, only a few perfumes are knwon which include 2-cyclopentyl cyclopentylcrotonate, mentioned above, and 2-cyclopentylcyclopentanone.

As for a cyclopentanone compound having two cyclopentyl derivative substituents, it is taught in Bull. Soc. Chim. Fr., (1973) 4(2), 1509 that, when cyclopentanone is treated with metallic sodium, 2-cyclopentylidenecyclopentanone and 2,5-dicyclopentylidenecyclopentanone are produced. But, this literature is silent on yield of the dipentylidene compound. Further it is taught in J. Am. Chem. Soc., (1974), 116, 1962 that, when cyclopentanone is heated in the presence of a zeolite in a toluene medium, 2-cyclopentylidenecyclopentanone and 2,5-dicyclopentylidenecyclopentanone are produced. The yield of 2,5-dicyclopentylidenecyclopentanone is only 8%. The two literatures are silent on the use of 2,5-dicyclopentylidenecyclopentanone as a perfume.

Further, it is described in Shin Jikken Kagaku Kouza, vol. 14 (II), p852 (published by Maruzen, Japan) that, when cyclopentanone is allowed to react with potassium hydroxide in an ethanol medium, 2,5-dicyclopentylidenecyclopentanone is produced in a yield of 12–51%. However, the inventors' experiments following the same procedures and conditions revealed that 2-cyclopentylidenecyclopentanone, i.e., a dimer of cyclopentanone, was preferentially produced and the yield of the target compound was below 1%. This literature is also silent on the use of the target compound as a perfume.

It is generally accepted that fragrances of compounds used as a perfume greatly vary even though there exists only a minor difference in chemical structure. Therefore, it is crucial for the development of novel perfumes to synthesize compounds having various substituents and closely examine fragrances of the compounds.

SUMMARY OF THE INVENTION

A primary object of the present invention is to provide a novel compound having a cyclopentanone structure or a cyclopentanol structure, which emits a floral or musk-tone fragrance.

Other objects of the present invention are to provide processes for producing the cyclopentanone or cyclopentanol compound, and a perfume composition comprising the same.

The present inventors have synthesized compounds with a cyclopentanone or cyclopentanol structure having introduced therein various cyclopentyl derivatives as substituent, and have closely examined fragrance of the cyclopentanone or cyclopentanol compounds. As the results of examination, it has been found that perfume compositions comprising a cyclopentanone or cyclopentanol compound having a specific cyclopentyl derivative substituent emit floral and powdery cosmetic-like fragrances and are useful for imparting the fragrances, and natural and fresh scent to variety of toiletries.

Thus, in a first aspect of the present invention, there is provided a composition comprising at least 60% by weight, based on the weight of the composition, of a cyclopentane compound having an oxygen-containing group and cyclopentylidene and/or cyclopentyl substituents, which is represented by the following general formula (1):

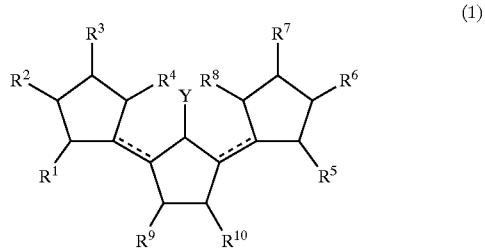

wherein ⋯⋯ independently represents a single bond or a double bond, $R^1$ through $R^{10}$ independently represent hydrogen or an alkyl group having 1 to 4 carbon atoms, and —Y is —OH or =O.

In a second aspect of the invention, there is provided a perfume composition comprising as a fragrant odor-emitting ingredient a cyclopentane compound having an oxygen-containing group and cyclopentilidene and/or cyclopentyl substituents, which is represented by the above formula (1).

In a third aspect of the invention, there is provided a process for preparing a 2,5-dicyclopentylidenecyclopentanone compound represented by the following general formula (4):

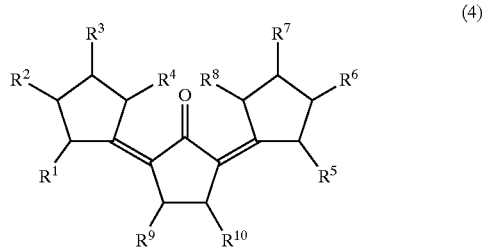

wherein $R^1$ through $R^{10}$ independently represent hydrogen or an alkyl group having 1 to 4 carbon atoms, which comprises allowing a 2-cyclopentylidenecyclopentanone compound represented by the following general formula (2):

(2)

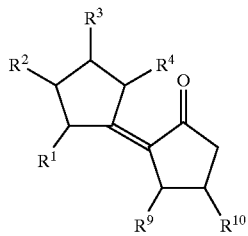

wherein $R^1$ through $R^4$, $R^9$ and $R^{10}$ independently represent hydrogen or an alkyl group having 1 to 4 carbon atoms, to react with a cyclopentanone compound represented by the following general formula (3):

(3)

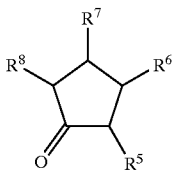

wherein $R^5$ through $R^8$ independently represent hydrogen or an alkyl group having 1 to 4 carbon atoms, under alkaline conditions.

In a fourth aspect of the invention, there is provided a process for preparing a 2,5-dicyclopentylcyclopentanone compound represented by the following general formula (5):

(5)

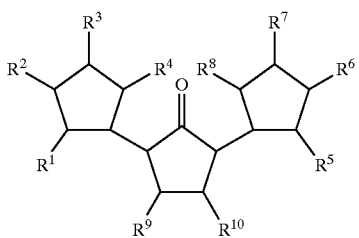

wherein $R^1$ through $R^{10}$ independently represent hydrogen or an alkyl group having 1 to 4 carbon atoms, which comprises reducing with hydrogen a 2,5-dicyclopentylidenecyclopentanone compound represented by the above formula (4).

In a fifth aspect of the invention, there is provided a process for preparing a 2,5-dicyclopentylidenecyclopentanol compound represented by the following general formula (6):

(6)

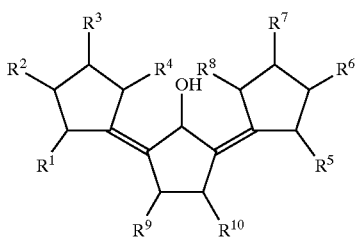

wherein $R^1$ through $R^{10}$ independently represent hydrogen or an alkyl group having 1 to 4 carbon atoms, which comprises reducing a 2,5-dicyclopentylidene-cyclopentanone compound represented by the above formula (4).

In a sixth aspect of the invention, there is provided a process for preparing a 2,5-dicyclopentylcyclopentanol compound represented by the following general formula (7):

(7)

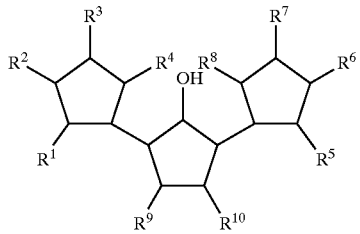

wherein $R^1$ through $R^{10}$ independently represent hydrogen or an alkyl group having 1 to 4 carbon atoms, which comprises reducing with hydrogen a 2,5-dicyclopentylcyclopentanone compound represented by the above formula (5).

In a seventh aspect of the invention, there is provided a process for preparing a 2,5-dicyclopentylcyclopentanol compound represented by the above formula (7), which comprises reducing with hydrogen a 2,5-dicyclopentylidenecyclopentanol compound represented by the above formula (6).

DESCRIPTION OF THE PREFERRED EMBODIMENTS

Composition Comprising Cyclopentane Compound Having Oxygen-Containing Group and Cyclopentylidene and/or Cyclopentyl Substituents, of Formula (1)

The cyclopentane compounds having an oxygen-containing group and cyclopentylidene and/or cyclopentyl substituents, which are represented by the above formula (1), are classified into two types, i.e., those which have a cyclopentanonol structure (in formula (1), —Y is —OH), and those which have a cyclopentanone structure (in formula (1), —Y is =O). These compounds of formula (1) have 2,5-dicyclopentylidene substituents; 2,5-dicyclopentyl substituents; or 2-cyclopentilidene-5-cyclopentyl substituents.

Among the compounds of formula (1), those in which —Y is —OH include, for example, 2,5-dicyclopentylcyclopentan-1-ol, 2-cyclopentylidene-5-cyclopentylcyclopentan-1-ol and 2,5-dicyclopentylidene-cyclopentan-1-ol. Of these, 2,5-dicyclopentylcyclopentan-1-ol is preferable.

Among the compounds of formula (1), those in which —Y is =O include, for example, 2,5-dicyclopentylcyclopentanone, 2-cyclopentylidene-5-cyclopentylcyclopentanone and 2,5-dicyclopentylidenecyclopentanone. Of these, 2,5-dicyclopentylcyclopentanone is preferable.

The composition of the invention comprises at least 60% by weight, based on the weight of the composition, of a the compound of formula (1). The purity of the compound of formula (1), i.e., the content thereof in the composition, can be 99% or more.

Preparation of Cyclopentane Compound Having Oxygen-Containing Group and Cyclopentylidene and/or Cyclopentyl Substituents, of Formula (1)

(i) Preparation of 2,5-Dicyclopentylidenecyclopentanone Compound of Formula (4)

A 2-cyclopentylidenecyclopentanone compound of formula (2), which is one raw material for the preparation of a compound of formula (4), i.e., a compound of formula (1) wherein Y is =O, is prepared by an ordinary procedure, namely, by an homoaldol reaction of a cyclopentanone compound followed by dehydration reaction.

As a base used for providing alkaline conditions under which a compound of formula (2) reacts with a compound of formula (3) for the synthesis of a compound of formula (4), there can be mentioned, for example, sodium methylate, sodium ethylate, potassium methylate, potassium ethylate, sodium hydroxide and potassium hydroxide. These bases may be used either alone or in combination. The amount of base is usually in the range of 0.1 to 2 moles, preferably 0.5 to 1.5 moles and more preferably 0.8 to 1.2 moles, per mole of a 2-cyclopentylidenecyclopentanone compound of formula (2).

A reaction medium used for the reaction of a compound of formula (2) with a compound of formula (3) for the synthesis of a compound of formula (4) is not particularly limited provided that the reaction medium is incapable of reacting with the base used. As examples of the reaction medium, there can be mentioned alcohols such as methanol and ethanol; aliphatic hydrocarbons such as hexane, heptane, octane, cyclopentane and cyclohexane; aromatic hydrocarbons such as benzene, toluene, ethylbenzene and xylene; and ethers such as diethyl ether, dibutyl ether, tetrahydrofuran and dioxane. These mediums may be used either alone or in combination. For example, a mixed medium of an alcohol with one or more other mediums can be mentioned.

The amount of a cyclopentanone compound of formula (3) used for the synthesis of a 2,5-dicyclopentylidenecyclopentanone compound of formula (4) is usually in the range of 0.1 to 2 moles, preferably 0.5 to 1.5 moles and more preferably 0.8 to 1.2 moles, per mole of a 2-cyclopentylidenecyclopentanone compound of formula (2).

The reaction temperature for the synthesis of a 2,5-dicyclopentylidenecyclopentanone compound of formula (4) is usually in the range of 20 to 180° C., preferably 40 to 140° C. and more preferably 60 to 100° C. The reaction pressure may be either reduced pressure or increased pressure. The reaction pressure is usually in the range of 0.5 to 2 atm, and preferably 0.8 to 1.2 atm.

After completion of the reaction for synthesis of a compound of formula (4), the reaction mixture is neutralized with an acid such as hydrochloric acid and is separated into an organic phase and an aqueous phase. The target compound is isolated and purified by a conventional procedure such as distillation and recrystallization.

(ii) Preparation of 2,5-Dicyclopentylcyclopentanone Compound of Formula (5), 2,5-Dicyclopentylidenecyclopentanol Compound of Formula (6), and 2,5-Dicyclopentylcyclopentanol Compound of Formula (7)

Hydrogen addition to the carbon—carbon double bonds of a 2,5-dicyclopentylidenecyclopentanone compound of formula (4) gives a 2,5-dicyclopentylcyclopentanone compound of formula (5), and reduction of the carbonyl group of the compound of formula (5) gives 2,5-dicyclopentylcyclopentanol compound of formula (7).

Reduction of the carbonyl group of a 2,5-dicyclopentylidenecyclopentanone compound of formula (4) gives 2,5-dicyclopentylidenecyclopentanol compound of formula (6), and hydrogen addition to the carbon—carbon double bonds of the compound of formula (6) gives 2,5-dicyclopentylcyclopentanol compound of formula (7).

The reduction reactions can be carried out by the conventional procedure. More specifically, reduction of a carbonyl group in the compound of formula (4) or the compound of formula (5) is preferably conducted by using, for example, sodium boron hydride (NaBH$_4$), lithium aluminum hydride (LiAlH$_4$) or di-isobutylaluminum hydride (iBu$_2$AlH). Hydrogen addition to carbon—carbon double bonds in the compound of formula (4) or the compound of formula (6) is preferably conducted according to a catalytic hydrogenation reduction using a catalyst such as palladium, ruthenium, rhodium, platinum or Raney nickel.

After completion of the reactions for the synthesis of compounds of formulae (5) to (7), when a catalytic reduction using a catalyst is conducted, the catalyst used is separated by filtration; and when the reduction using NaBH$_4$, LiAlH$_4$ or iBu$_2$AlH is conducted, the reaction mixture is neutralized with an acid, for example, hydrochloric acid, and then an organic phase is separated from an aqueous phase. The target compounds are isolated and purified by conventional means such as distillation and recrystallization.

Perfume Composition

The composition of the invention comprising at least 60% by weight, based on the weight of the composition, of the compound of (1) are used as a perfume composition. Among the compounds of formula (1); cyclopentanol compounds of formulae (6) and (7) and cyclopentanone compounds of formula (5) emit floral and powdery cosmetic-like fragrances and are preferable ingredients in perfume compositions. These compounds may be used either alone or in combination. 2,5-Dicyclopentylcyclopentanone of the formula shown in Example 2 below, and 2,5-dicyclopentylcyclopentanol of the formula shown in Example 5 below, emit a sweet floral or tropical fruity musk-tone fragrance, have a powerful and long-lasting musk effect, and are discoloring; and are especially preferable ingredients in perfume compositions.

A perfume composition comprising at least one compound selected from the compounds of formula (1) is useful for imparting fragrances to, for example, a perfume, a soap, a shampoo, a hair-treatment, a body shampoo, a detergent, a cosmetic, a hair-spray and an aromatic.

According to the need, conventional fragrance/flavor-imparting agents and fragrance/flavor-retaining agents can be incorporated in combination with the compound of formula (1) in the perfume composition of the invention. Auxiliaries, diluents and other additives such as enzymes, colorants, antioxidants, preservatives, germicides can also be incorporated. Further, nourishing and repairing agents such as crude drugs, vitamins, nutrients, and fats and fatty oils, and modifiers such as bleaching agents, deodorizers and softeners, can also be incorporated in combination with the compound of formula (1) in the perfume composition of the invention.

The invention will now be described specifically by the following examples that by no means limit the scope of the invention.

EXAMPLE 1

Preparation of 2,5-dicyclopentylidenecyclopentanone Represented by the Following Formula:

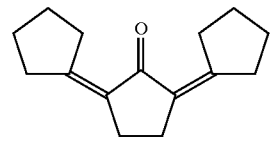

A one-liter four-necked flask equipped with a stirrer, a reflux condenser, a dropping funnel and a thermometer was charged with 96.5 g (0.5 mole) of 28% sodium methylate and 200 ml of ethylbenzene, and the temperature of the content was elevated to 80° C. with stirring. When 30 minutes elapsed, 75.1 g (0.5 mole) of 2-cyclopentylidenecyclopentanone was added over a period of 20 minutes, and stirring was continued further for 30 minutes. Then 42.1 g (0.5 mole) of cyclopentanone was added over a period of 15 minutes, and stirring was continued further for 6 hours. The reaction mixture was neutralized with 200 g (0.55 mole) of 10% hydrochloric acid, and an organic phase was separated from an aqueous phase. Distillation of the organic phase for removing the solvent and unreacted raw materials gave 63.7 g of a crude target compound having a purity of 78.6% (yield: 58%). This compound was dissolved in 120 g of ethanol maintained at 80° C., and then cooled to 25° C., and 60 g of water was added to effect recrystallization, followed by filtration. 42.9 g of a target compound having a purity of 92.2% was obtained (yield: 39%).

EXAMPLE 2

Preparation of 2,5-dicyclopentylcyclopentanone Represented by the Following Formula:

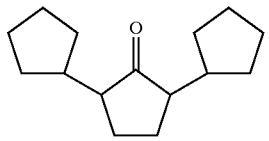

A one-liter three-necked flask equipped with a stirrer, a reflux condenser and a thermometer was charged with 160 g (0.74 mole) of 2,5-dicyclopentylidenecyclopentanone, 480 g of ethanol and 0.80 g of 5%Pd/C. The content was flushed with nitrogen three times and then with hydrogen three times. Stirring was continued at 25–35° C. for 8 hours, and then the catalyst was removed by filtration and the solvent was distilled off. Distillation of the product gave 106 g of a target compound having a purity of 99.5% (yield: 65%).

EXAMPLE 3

Preparation of 2,5-dicyclopentylidenecyclopentan-1-ol Represented by the Following Formula:

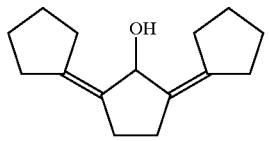

A 300 ml four-necked flask equipped with a stirrer, a reflux condenser, a dropping funnel and a thermometer was charged with 36 g (0.25 mole) of diisobutylaluminum hydride and 100 ml of toluene. While the content was stirred at a temperature of 30 to 40° C., 50 ml of a solution in toluene of 54 g (0.25 mole) of 2,5-dicyclopentylidenecyclopentanone was added over a period of 30 minutes, and stirring was continued further for 6 hours. The thus-obtained reaction mixture was incorporated in 200 g (0.2 mole) of 4% hydrochloric acid, and an organic phase was separated from an aqueous phase. Distillation of the organic phase for removing the solvent gave 41.3 g of a crude target compound having a purity of 86% (yield: 76%). This compound was dissolved in 100 g of ethanol maintained at 80° C., and then cooled to 25° C., and 50 g of water was added to effect recrystallization, followed by filtration. 37.1 g of a target compound having a purity of 98.2% was obtained (yield: 68%).

EXAMPLE 4

Preparation of 2,5-dicyclopentylcyclopentan-1-ol Represented by the Following Formula:

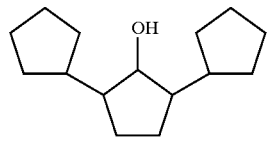

A 300 ml four-necked flask equipped with a stirrer, a reflux condenser, a dropping funnel and a thermometer was charged with 5 g (0.13 mole) of sodium boron hydride and 100 ml of ethanol. While the content was stirred at a temperature of 30 to 40° C., 56 g (0.25 mole) of 2,5-dicyclopentylcyclopentanone was added over a period of 35 minutes, and stirring was continued further for 15 hours. The thus-obtained reaction mixture was incorporated in 200 g (0.2 mole) of 4% hydrochloric acid, and subjected to extraction using 150 ml of toluene. An organic phase was separated from an aqueous phase. The solvent was distilled off from the organic phase and the thus-obtained crude target compound was dissolved in 200 ml of ethanol. The ethanol solution of the target compound was added in 200 ml of water with stirring. The thus-obtained white crystal was filtered and dried to give 46 g (0.21 mole) of a target compound having a purity of 99% (yield: 81%).

This high-purity target compound emits a gardenia-like sweet floral fragrance, and can be used for perfume preparations having, for example, gardenia, gingerlily, honeysuckle, jasmin, lilac and tuberose fragrances.

EXAMPLE 5

Preparation of 2,5-dicyclopentylcyclopentan-1-ol Represented by the Following Formula:

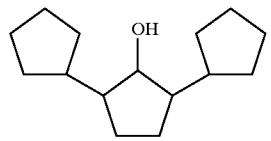

A one-liter four-necked flask equipped with a stirrer, a reflux condenser, a dropping funnel and a thermometer was charged with 109 g (0.5 mole) of 2,5-dicyclopentylidenecyclopentanon-1-ol, 400 g of ethanol and 0.5 g of 5% Pd/C. The content was flushed with nitrogen three times and then with hydrogen three times. Stirring was continued at 25–35° C. for 8 hours, and then the catalyst was removed by filtration and the solvent was distilled off. The thus-obtained crude target compound was dissolved in 400 ml of ethanol. The ethanol solution of the target compound was added in 400 ml of water with stirring. The thus-obtained white crystal was filtered and dried to give 92 g (0.42 mole) of a target compound having a purity of 99% (yield: 84%).

EXAMPLE 6

Preparation and Evaluation of Perfume Preparations

To a control fresh green floral-type perfume preparation for a body shampoo, which had the recipe shown in Table 1, 10 parts by weight of 2,5-dicyclopentylcyclopentan-1-ol of formula (7), prepared in Example 5, was added to prepare a novel perfume preparation of the invention.

TABLE 1

Fresh Green Floral Type Perfume Preparations

| Ingredients (parts by weight) | Control | Invention (Compound of Example 5) |
|---|---|---|
| Linalyl acetate | 2 | 2 |
| Helional (IFF) | 2 | 2 |
| Styrallyl acetate | 4 | 4 |
| Methyl anthranilate | 4 | 4 |
| Dihydromyrcenol | 10 | 10 |
| Cis-3-hexenyl salicylate | 70 | 70 |
| 2, 5-Dicyclopentylcyclopentan-1-ol | — | 10 |
| Dimethylbenzylcarbinyl acetate | 10 | 10 |
| Terpineol | 10 | 10 |
| Benzyl acetate | 30 | 30 |
| Lilial (Givaudan) | 40 | 40 |
| Phenylethyl alcohol | 50 | 50 |
| Lyral (IFF) | 140 | 140 |
| CLAIGEON (Zeon Corp.) | 150 | 150 |
| Eugenol | 10 | 10 |
| Methyl ionone | 30 | 30 |
| Isocamphyl cyclohexanol | 30 | 30 |
| Acetyl cedrene | 40 | 40 |
| Galoxolide (IFF) | 60 | 60 |
| Diethyl phthalate | 268 | 258 |
| Tonalide (PFW) | 40 | 40 |
| Total | 1,000 | 1,000 |

Note: Parenthesized term is name of maker

The perfume preparation of the invention had an elegant, sweet and deep floral fragrance in addition to the top note of a fresh floral green scent inherently possessed by the control perfume preparation.

An organoleptic test of the perfume preparations was conducted by seven panelists. The test results are shown in Table 2.

TABLE 2

Results of Organoleptic Examination

| Panelist | Control | Invention Compound of Example 5 |
|---|---|---|
| A | Sour scent came floating in | Calm faint fragrance |
| B | Strong chemical scent | Sweet and powdery cosmetic-like scent; natural and fresh sweet fragrance |
| C | Strong scent | Elegant floral scent |
| D | Strong hand-cream-like scent | Better than control preparation |
| E | Weak sweet fragrance | Fine scent came up |
| F | Powerful scent | Mild and elegant sweet fragrance; high-grade scent |
| G | Non-deep scent | Deep, elegant and harmonious scent |

What is claimed is:

1. A perfume composition comprising as a fragrant odor-emitting ingredient a cyclopentane compound having an oxygen-containing group and cyclopentylidene and/or cyclopentyl substituents, said perfume composition comprising:

at least 60% by weight, based on the weight of the composition, of the cyclopentane compound having an oxygen-containing group and cyclopentylidene and/or cyclopentyl substituents, which is represented by the following general formula (1):

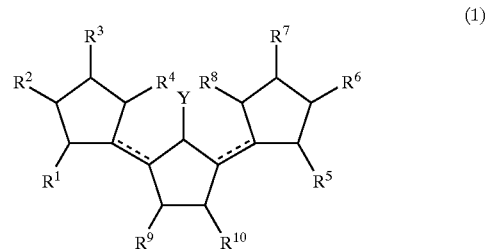

(1)

wherein ------ independently represents a single bond or a double bond, $R^1$ through $R^{10}$ independently represent hydrogen or an alkyl group having 1 to 4 carbon atoms, and —Y is —OH or =O; and an additive selected from the group consisting of enzymes, colorants, antioxidants, preservatives, germicides, crude drugs, vitamins, nutrients, fats, fatty oils, bleaching agents, deodorizers and softeners.

2. The perfume composition according to claim 1, wherein the cyclopentane compound having an oxygen-containing group and cyclopentylidene and/or cyclopentyl substituents is at least one compound selected from the group consisting of 2,5-dicyclopentylcyclopentanone compounds represented by the following general formula (5):

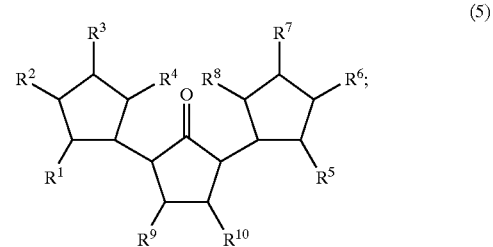

(5)

2,5-dicyclopentylidenecyclopentanol compounds represented by the following general formula (6):

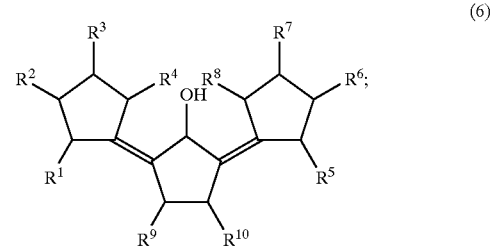

(6)

and 2,5-dicyclopentylcyclopentanol compounds represented by the following general formula (7):

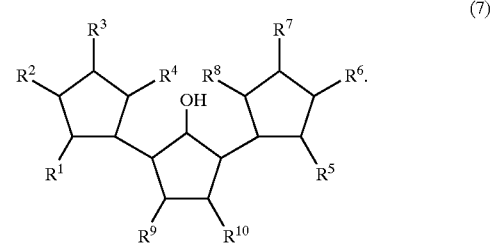

(7)

3. The perfume composition according to claim 1, wherein said cyclopentane compound is a 2,5-dicyclopentylidene-cyclopentanone compound represented by the following formula (4):

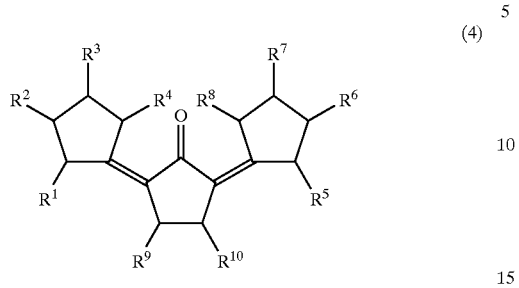

(4)

wherein $R^1$ through $R^{10}$ independently represent hydrogen or an alkyl group having 1 to 4 carbon atoms, and which is prepared by allowing a 2-cyclopentylidenecyclopentanone compound represented by the following general formula (2):

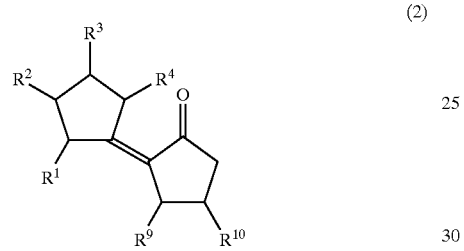

(2)

wherein $R^1$ through $R^4$, $R^9$ and $R^{10}$ independently represent hydrogen or an alkyl group having 1 to 4 carbon atoms, to react with a cyclopentanone compound represented by the following general formula (3):

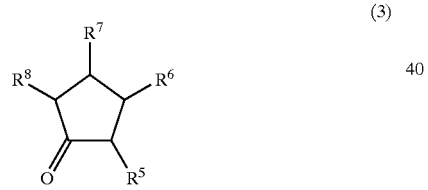

(3)

wherein $R^5$ through $R^8$ independently represent hydrogen or an alkyl group having 1 to 4 carbon atoms, under alkaline conditions.

4. The perfume composition according to claim 1, wherein said cyclopentane compound is 2,5-dicyclopentyl-cyclopentanone compound represented by the following general formula (5):

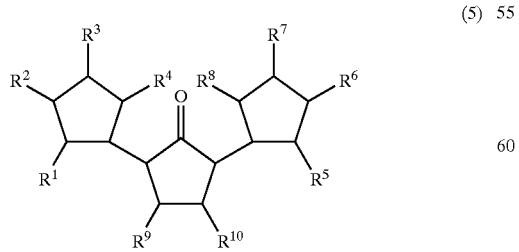

(5)

wherein $R^1$ through $R^{10}$ independently represent hydrogen or an alkyl group having 1 to 4 carbon atoms, and which is prepared by reducing with hydrogen a 2,5-dicyclopentylidenecyclopentanone compound represented by the following general formula (4):

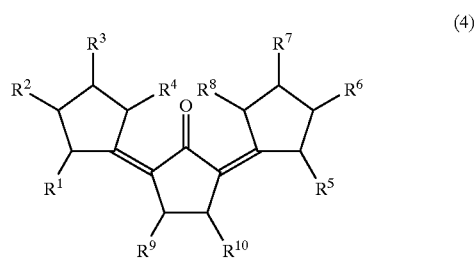

(4)

wherein $R^1$ through $R^{10}$ are the same as defined above for the formula (5).

5. The perfume composition according to claim 1, wherein said cyclopentane compound is a 2,5-dicyclopentylidene-cyclopentanol compound represented by the following general formula (6):

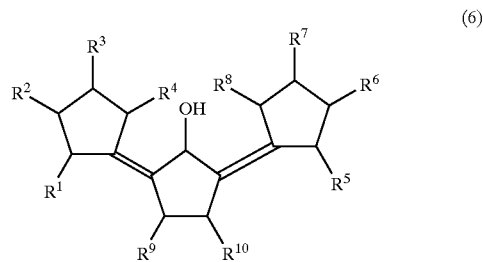

(6)

wherein $R^1$ through $R^{10}$ independently represent hydrogen or an alkyl group having 1 to 4 carbon atoms, and which is prepared by reducing a 2,5-dicyclopentylidenecyclopentanone compound represented by the following general formula (4):

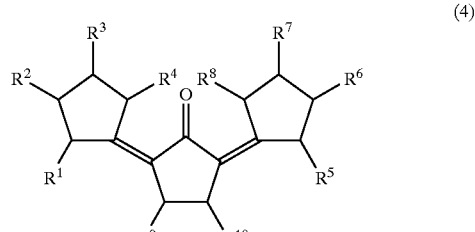

(4)

wherein $R^1$ through $R^{10}$ are the same as defined above for the formula (6).

6. The perfume composition according to claim 1, wherein said cyclopentane compound is a 2,5-dicyclopentyl-cyclopentanol compound represented by the following general formula (7):

(7)

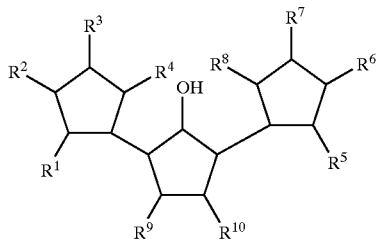

wherein $R^1$ through $R^{10}$ independently represent hydrogen or an alkyl group having 1 to 4 carbon atoms, and which is prepared by reducing with hydrogen a 2,5-dicyclopentylcyclopentanone compound represented by the following general formula (5):

(5)

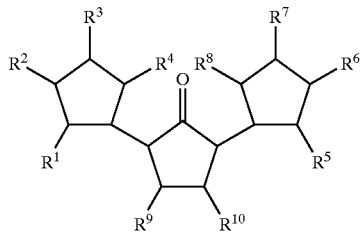

wherein $R^1$ through $R^{10}$ are the same as defined above for the formula (7).

7. The perfume composition according to claim 1, wherein said cyclopentane compound is a 2,5-dicyclopentyl-cyclopentanol compound represented by the following general formula (7):

(7)

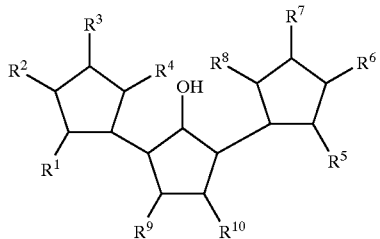

wherein $R^1$ through $R^{10}$ independently represent hydrogen or an alkyl group having 1 to 4 carbon atoms, which comprises reducing with hydrogen a 2,5-dicyclopentylidenecyclopentanol compound represented by the following general formula (6):

(6)

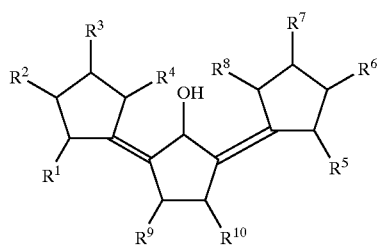

wherein $R^1$ through $R^{10}$ are the same as defined above for the formula (7).

8. A fragrance-imparting method comprising incorporating a composition comprising at least 60% by weight, based on the weight of the composition, of a cyclopentane compound having an oxygen-containing group and cyclopentylidene and/or cyclopentyl substituents, which is represented by the following general formula (1):

(1)

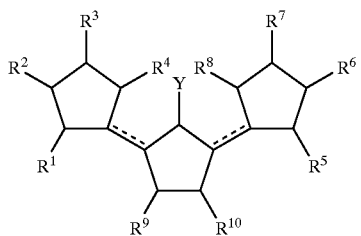

wherein ----- independently represents a single bond or a double bond, wherein $R^1$ through $R^{10}$ independently represent hydrogen or an alkyl group having 1 to 4 carbon atoms, and —Y is —OH or =O, into a perfume, a soap, a shampoo, a hair-treatment, a body shampoo, a detergent, a cosmetic, a hair-spray or an aromatic.

9. A fragrance-imparting method comprising incorporating the perfume composition as claimed in claim 1, into a perfume, a soap, a shampoo, a hair-treatment, a body shampoo, a detergent, a cosmetic, a hair-spray or an aromatic.

\* \* \* \* \*